United States Patent
Derrick

(10) Patent No.: US 6,911,555 B2
(45) Date of Patent: Jun. 28, 2005

(54) CYCLIC NITROMETHYL ACETIC ACID DERIVATIVES

(75) Inventor: Andrew Michael Derrick, Ramsgate (GB)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 10/677,837

(22) Filed: Oct. 2, 2003

(65) Prior Publication Data

US 2004/0116525 A1 Jun. 17, 2004

Related U.S. Application Data

(60) Provisional application No. 60/421,867, filed on Oct. 28, 2002.

(30) Foreign Application Priority Data

Oct. 4, 2002 (GB) .............................................. 0223072

(51) Int. Cl.[7] ........................ C07C 25/10; A61K 31/195
(52) U.S. Cl. ....................................... 562/501; 514/561
(58) Field of Search .......................... 562/501; 514/561, 514/573

(56) References Cited

FOREIGN PATENT DOCUMENTS

| EP | 01400214.1 | 7/2004 |
|----|------------|--------|
| WO | WO 99/21824 | 5/1999 |
| WO | WO 01/28978 | 4/2001 |
| WO | WO 02/85839 | 10/2002 |

OTHER PUBLICATIONS

Chen, L., et al, "Study of Chiral Auxiliaries for the Intramolecular [2+2] Cycloaddition of a Keteniminium Salt to an Olefinic Double Bond. A New Asymmetric Synthesis of Cyclobutanones", Tetrahedron Letters, vol. 31, No. 31, 1990; pp 4467–4470.

Hoffman, H.M.R., et al, "Synthesis of Cyclogutylideneacetic Esters Via Aluminum Chloride Promoted [2+2] Cycloadditions of Ethyl 2,3–Butadienoate to Olefins", Tetrahedron Letters, vol. 22, No. 21, 1981; pp 1953–1956.

Houge, C., et al, "Modes for Assymetric [2+2] Cycloadditions", J. Am. Chem. Soc., 1982, 104; pp 2920–2921.

*Primary Examiner*—Cecilia J. Tsang
*Assistant Examiner*—Taylor Victor Oh
(74) *Attorney, Agent, or Firm*—Suzanne M. Harvey; David R. Kurlandsky; Charles W. Ashbrook

(57) ABSTRACT

The invention provides salts of formula (I)

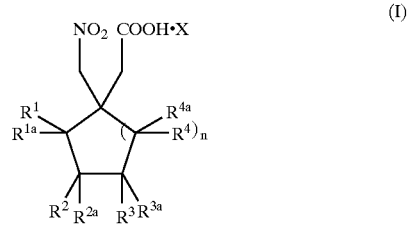

wherein X is a basic counterion selected from a group I or group II metal and a primary, secondary or tertiary amine; n is 0, 1 or 2; and $R^1$, $R^{1a}$, $R^2$, $R^{2a}$, $R^3$, $R^{3a}$, $R^4$ and $R^{4a}$ are independently selected from H and $C_1$–$C_6$ alkyl, or $R^1$ and $R^2$ or $R^2$ and $R^3$ are taken together to form a $C_3$–$C_7$ cycloalkyl ring, which is optionally substituted with one or two substituents selected from $C_1$–$C_6$ alkyl, which are useful as intermediates in the preparation of cyclic and bicyclic amino acids. Processes for the preparation of the final products and for the conversion of the compounds of formula (I) to amino acids are included.

5 Claims, No Drawings

CYCLIC NITROMETHYL ACETIC ACID DERIVATIVES

This United States Utility Application claims the benefit of United Kingdom Application Number 0223072.0 filed Oct. 4, 2002 and U.S. Provisional Application No. 60/421,867 filed Oct. 28, 2002.

FIELD OF THE INVENTION

This invention relates to novel salts of cyclic nitromethyl acetic acid derivatives, to processes for their production, and to their use as intermediates in the preparation of cyclic amino acids.

BACKGROUND TO THE INVENTION

International Patent Application Publication No. WO 99/21824 discloses cyclic amino acids that are useful in the treatment of epilepsy, faintness attacks, neurodegenerative disorders, depression, anxiety, panic, pain, neuropathological disorders, gastrointestinal disorders such as irritable bowel syndrome (IBS) and inflammation, especially arthritis. The compounds disclosed include those of the formula:

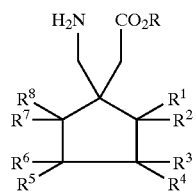

and salts thereof, in which: R is hydrogen or a lower alkyl; and $R^1$ to $R^8$ are each independently selected from hydrogen, alkyl of from 1 to 6 carbons, phenyl, benzyl, fluorine, chlorine, bromine, hydroxy, hydroxymethyl, amino, aminomethyl, trifluoromethyl, —$CO_2H$, —$CO_2R^{15}$, —$CH_2CO_2H$, —$CH_2CO_2R^{15}$, —$OR^{15}$ wherein $R^{15}$ is a alkyl of from 1 to 6 carbons, phenyl, or benzyl, $R^1$ to $R^8$ not being simultaneously hydrogen.

International Patent Application Publication No. WO01/28978, corresponding to U.S. patent application Ser. No. 60/160725, describes a series of novel bicyclic amino acids, their pharmaceutically acceptable salts, and their prodrugs of formula:

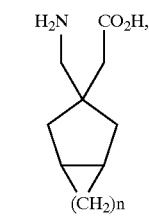

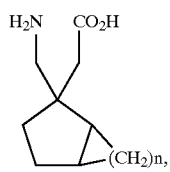

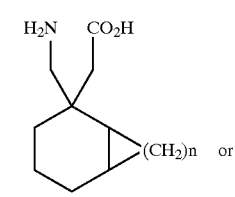

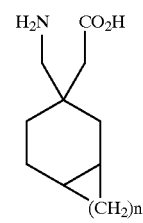

wherein n is an integer of from 1 to 4, where there are stereocentres, each center may be independently R or S, preferred compounds being those of Formulae I–IV above in which n is an integer of from 2 to 4. The compounds are disclosed as being useful in treating a variety of disorders including epilepsy, faintness attacks, hypokinesia, cranial disorders, neurodegenerative disorders, depression, anxiety, panic, pain, neuropathological disorders, and sleep disorders.

Patent application No. EP 01400214.1 discloses the use of compounds of formula I to IV above for the prevention and treatment of visceral pain, and gastrointestinal disorders.

More recently, International Patent Application No. PCT/IB02/01146 (unpublished at the priority date of the present invention, published as WO02/85839) describes cyclic amino acids of formulae (I)–(XXV):

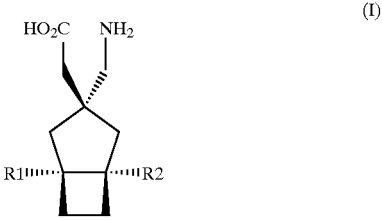

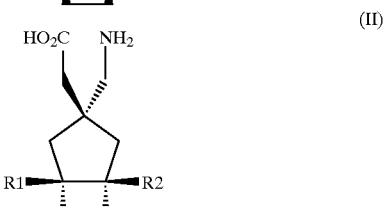

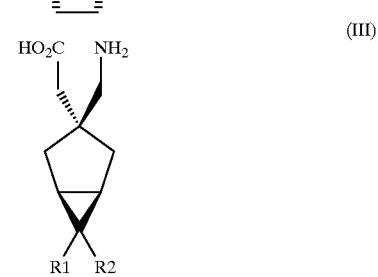

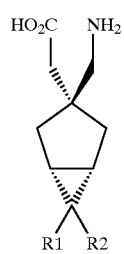
(IV)
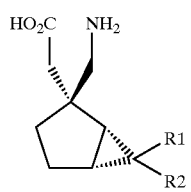
(V)
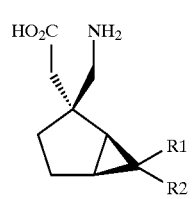
(VI)
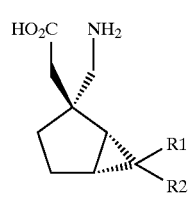
(VII)
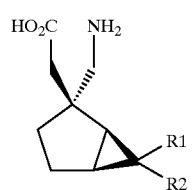
(VIII)
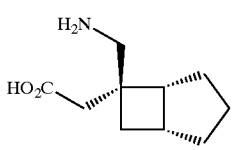
(IX)
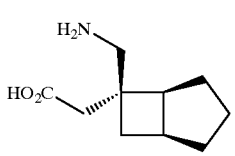
(X)
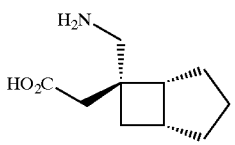
(XI)
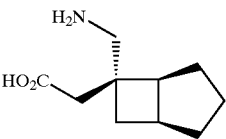
(XII)
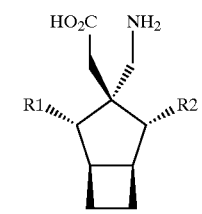
(XIII)
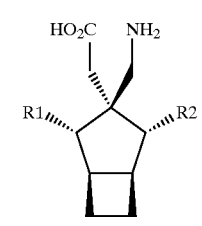
(XIV)
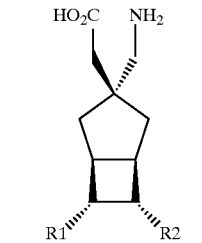
(XV)
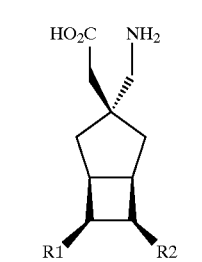
(XVI)
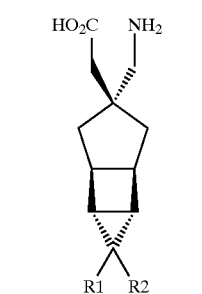
(XVII)
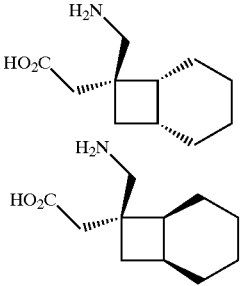
XVIII
XIX

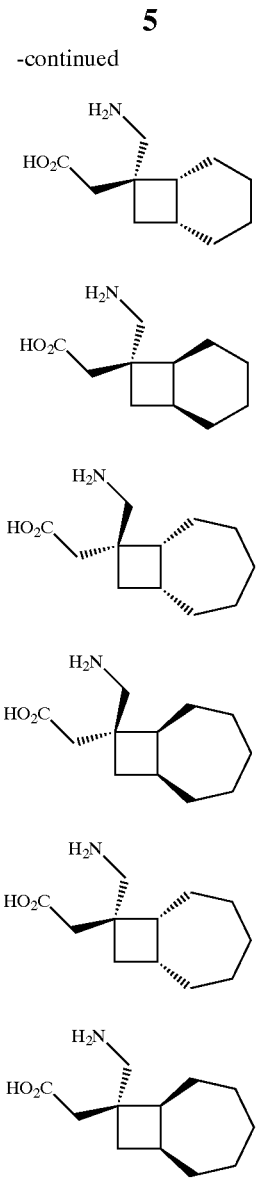

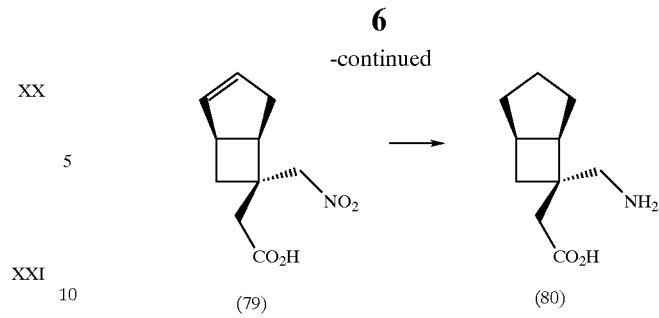

The application also discloses, as Method F, preparation of the following compounds:

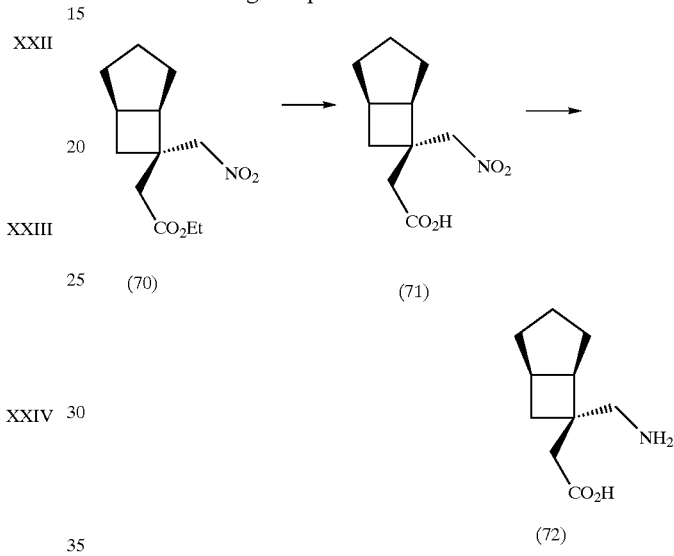

The compound of formula (70) may be prepared by Method A described in PCT/IB02/01146, illustrated here from compound (9), a known compound, see L. Y. Chen, L. Ghosez, *Tetrahedron Letters*, 1990, 31, 4467; C. Houge, A. M. Frisque-Hesbain, A. Mockel, L. Ghosez, J. P. Declercq, G. Germain, M. Van Meerssche, J. Am. Chem. Soc., 1982, 104, 2920.

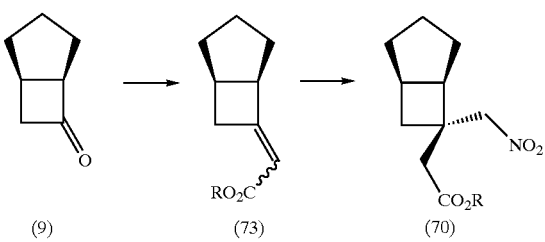

Compounds of formula (73) have been described in Hoffmann, H. M. R.; Ismail, Zeinhom M.; Weber, Anette. Dep. Chem., Univ. Hannover, Hannover, Fed. Rep. Ger. Tetrahedron Lett. (1981), 22(21), 1953–6.

The inventors have found that difficulties may exist in the isolation and purification of the nitro acid analogues of the cyclic amino acids described in the prior art, such as compounds of formula 71, and have discovered that the nitro acid salt derivatives of the present invention, being crystalline and having good stability, are particularly useful for improved isolation and purification.

wherein $R^1$ and $R^2$ are each independently selected from H, straight or branched alkyl of 1–6 carbon atoms, cycloalkyl of from 3–6 carbon atoms, phenyl and benzyl, subject to the proviso that, except in the case of a tricyclooctane compound of formula (XVII), $R^1$ and $R^2$ are not simultaneously hydrogen; for use in the treatment of a number of indications, including pain. The application discloses, as Method H, preparation of the following compounds:

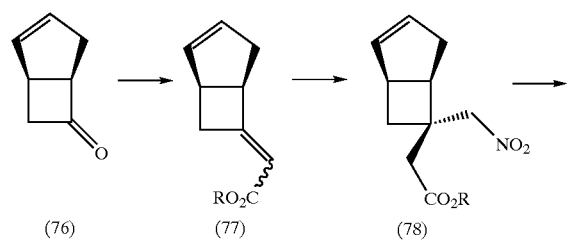

SUMMARY OF THE INVENTION

The invention provides salts of cyclic and bicyclic nitromethyl acetic acid derivatives of formula (I):

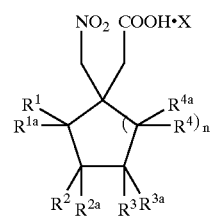

(I)

wherein X is a basic counterion selected from a group I or group II metal and a primary, secondary or tertiary amine;

n is 0, 1 or 2; and $R^1$, $R^{1a}$, $R^2$, $R^{2a}$, $R^3$, $R^{3a}$, $R^4$ and $R^{4a}$ are independently selected from H and $C_1$–$C_6$ alkyl, or $R^1$ and $R^2$ or $R^2$ and $R^3$ are taken together to form a $C_3$–$C_7$ cycloalkyl ring, which is optionally substituted with one or two substituents selected from $C_1$–$C_6$ alkyl.

Preferably X is selected from sodium, cinchonidine, cyclohexylamine, R-alpha-methylbenzylamine, S-alpha-methylbenzylamine and S-1-cyclohexylethylamine.

Suitably, $R^1$, $R^{1a}$, $R^{2a}$, $R^{3a}$, $R^4$ and $R^{4a}$ are H and $R^2$ and $R^3$ are independently selected from H and methyl, or $R^{1a}$, $R^{2a}$, $R^{3a}$ and $R^{4a}$ are H and $R^1$ and $R^2$ or $R^2$ and $R^3$ are taken together to form a $C_3$–$C_7$ cycloalkyl ring, which is optionally substituted with one or two methyl substituents.

Preferably, $R^1$, $R^{1a}$, $R^{2a}$, $R^{3a}$, $R^4$ and $R^{4a}$ are H and $R^2$ and $R^3$ are independently selected from H and methyl, or $R^{1a}$, $R^{2a}$, $R^{3a}$ and $R^{4a}$ are H and $R^1$ and $R^2$ or $R^2$ and $R^3$ are taken together to form a $C_4$–$C_5$ cycloalkyl ring.

Preferably, when n is 0, $R^1$, $R^{1a}$, $R^{2a}$, $R^{3a}$, $R^4$ and $R^{4a}$ are H and $R^2$ and $R^3$ form a cyclopentyl ring.

Preferably, when n is 1, $R^1$, $R^{1a}$, $R^{2a}$, $R^{3a}$, $R^4$ and $R^{4a}$ are H and $R^2$ and $R^3$ are both methyl or $R^1$, $R^{1a}$, $R^{2a}$, $R^{3a}$, $R^4$ and $R^{4a}$ are H and $R^2$ and $R^3$ form a cyclobutyl ring.

Preferably, when n is 2, $R^1$, $R^{1a}$, $R^2$, $R^{2a}$, $R^3$, $R^{3a}$, $R^4$ and $R^{4a}$ are H.

Most preferably, n is 0, $R^1$, $R^{1a}$, $R^{2a}$, $R^{3a}$, $R^4$ and $R^{4a}$ are H and $R^2$ and $R^3$ form a cyclopentyl ring.

Suitable compounds are selected from compounds of formula II–V:

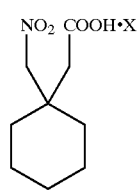

(II)

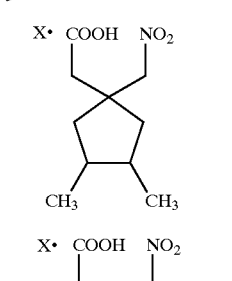

(III)

(IV)

(V)

wherein X is as defined above.

Preferred compounds are selected from compounds of formula (II), (IIIa), (IVa) and (Va):

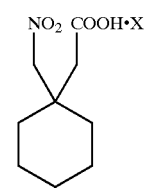

(II)

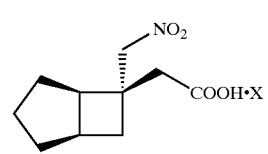

(IIIa)

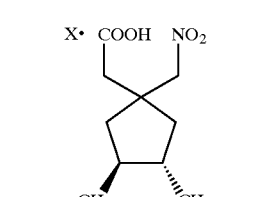

(IVa)

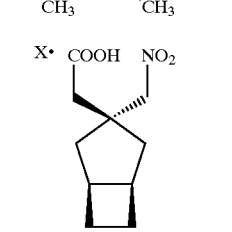

(Va)

wherein X is as defined above.

A suitable subgroup according to the present invention is represented by a compound of formula (Ia):

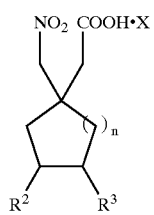

(Ia)

wherein X is a basic counterion selected from a group I or group II metal and a primary, secondary or tertiary amine; and either n is 0 and $R^2$ and $R^3$ form a cyclopentyl ring, or
n is 1 and $R^2$ and $R^3$ represent methyl or together form a cyclobutyl ring, or
n is 2 and $R^2$ and $R^3$ are H.

Particularly preferred compounds of formula (I) are:
(1RS,5RS,6SR)-[6-(nitromethyl)bicyclo[3.2.0]hept-6-yl] acetic acid cyclohexylamine salt;
(1R,5R,6S)-[6-(nitromethyl)bicyclo[3.2.0]hept-6-yl]acetic acid cyclohexylamine salt;
(1RS,5RS,6SR)-[6-(nitromethyl)bicyclo[3.2.0]hept-6-yl] acetic acid (R)-α-methylbenzylamine salt,
(1R,5R,6S)-[6-(nitromethyl)bicyclo[3.2.0]hept-6-yl]acetic acid (R)-α-methylbenzylamine salt;
(1RS,5RS,6SR)-[6-(nitromethyl)bicyclo[3.2.0]hept-6-yl] acetic acid sodium salt;
(1R,5R,6S)-[6-(nitromethyl)bicyclo[3.2.0]hept-6-yl]acetic acid sodium salt;
(1RS,5RS,6SR)-[6-(nitromethyl)bicyclo[3.2.0]hept-6-yl] acetic acid (S)-α-methylbenzylamine salt;
(1R,5R,6S)-[6-(nitromethyl)bicyclo[3.2.0]hept-6-yl]acetic acid (S)-α-methylbenzylamine salt;
(1RS,5RS,6SR)-[6-(nitromethyl)bicyclo[3.2.0]hept-6-yl] acetic acid (S)-1-cyclohexylethylamine salt;
(1R,5R,6S)-[6-(nitromethyl)bicyclo[3.2.0]hept-6-yl]acetic acid (S)-1-cyclohexylethylamine salt;
(1RS,5RS,6SR)-[6-(nitromethyl)bicyclo[3.2.0]hept-6-yl] acetic acid cinchonidine salt; and
(1R,5R,6S)-[6-(nitromethyl)bicyclo[3.2.0]hept-6-yl]acetic acid cinchonidine salt;

The invention further provides the use of compounds of formula (I) as intermediates in the preparation of compounds of formula (VI);

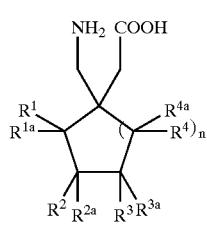

(VI)

wherein n is 0, 1 or 2; and
$R^1$, $R^{1a}$, $R^2$, $R^{2a}$, $R^3$, $R^{3a}$, $R^4$ and $R^{4a}$ are independently selected from H and $C_1$–$C_6$ alkyl, or
$R^1$ and $R^2$ or $R^2$ and $R^3$ are taken together to form a $C_3$–$C_7$ cycloalkyl ring, which is optionally substituted with one or two substituents selected from $C_1$–$C_6$ alkyl.

Suitably, the compound of formula (VI) prepared from a compound of formula (I) is gabapentin, (1R,5R,6S)-[6-(aminomethyl)bicyclo[3.2.0]hept-6-yl]acetic acid, aminomethyl-3,4-dimethyl-cyclopentyl)-acetic acid or (1α, 3α,5α)(3-amino-methyl-bicyclo[3.2.0]hept-3-yl)-acetic acid.

Preferably, the compound of formula (VI) prepared from a compound of formula (I) is (1R,5R,6S)-[6-(aminomethyl) bicyclo[3.2.0]hept-6-yl]acetic acid.

As a further aspect, the invention provides the compound (1α,3α,5α)(3-nitromethyl-bicyclo[3.2.0]hept-3-yl)-acetic acid.

As a yet further aspect, the invention provides the use of (1α,3α,5α)(3-nitromethyl-bicyclo[3.2.0]hept-3-yl)-acetic acid as an intermediate in the preparation of (1α,3α,5α)(3-amino-methyl-bicyclo[3.2.0]hept-3-yl)-acetic acid.

In the above definitions, alkyl groups containing the requisite number of carbon atoms, except where indicated, can be unbranched- or branched-chain. Examples of alkyl include methyl, ethyl, n-propyl, i-propyl, n-butyl, i-butyl, sec-butyl and t-butyl. A cycloalkyl group refers to a saturated mono carbocyclic ring.

The compounds of the present invention possess one or more chiral centers and each center may exist in the R(D) or S(L) configuration. The present invention includes all enantiomeric and epimeric forms as well as the appropriate mixtures thereof. Separation of diastereoisomers or cis and trans isomers may be achieved by conventional techniques, e.g. by fractional crystallisation, chromatography or H.P.L.C. of a stereoisomeric mixture of a compound of the invention or a suitable salt or derivative thereof. An individual enantiomer of a compound of the invention may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

The compounds of formula (VI) are useful as agents for treating or relieving the symptoms of neurodegenerative disorders. Such neurodegenerative disorders include, for example, Alzheimer's disease, Huntington's disease, Parkinson's disease, and Amyotrophic Lateral Sclerosis. The present invention also covers treating neurodegenerative disorders termed acute brain injury. These include but are not limited to: stroke, head trauma, and asphyxia. Stroke refers to a cerebral vascular disease and may also be referred to as a cerebral vascular accident (CVA) and includes acute thromboembolic stroke. Stroke includes both focal and global ischemia. Also, included are transient ischemic attacks and other cerebral vascular problems accompanied by cerebral ischemia. These vascular disorders may occur in a patient undergoing carotid endarterectomy specifically or other cerebrovascular or vascular surgical procedures in general, or diagnostic vascular procedures including cerebral angiography and the like. Other incidents are head trauma, spinal cord trauma, or injury from general anoxia, hypoxia, hypoglycemia, hypotension as well as similar injuries seen during procedures from embole, hyperfusion, and hypoxia. The instant invention would be useful in a range of incidents, for example, during cardiac bypass surgery, in incidents of intracranial hemorrhage, in perinatal asphyxia, in cardiac arrest, and status epilepticus.

The compounds of formula (VI) are useful for the general treatment of pain, particularly neuropathic pain. Physiological pain is an important protective mechanism designed to warn of danger from potentially injurious stimuli from the external environment. The system operates through a specific set of primary sensory neurones and is exclusively activated by noxious stimuli via peripheral transducing mechanisms (Millan 1999 Prog. Neurobio. 57: 1–164 for an integrative Review). These sensory fibres are known as nociceptors and are characterised by small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred after complex processing in the dorsal horn, either directly or via brain stem relay nuclei to the ventrobasal thalamus and then on to the cortex, where the sensation of pain is generated.

Intense acute pain and chronic pain may involve the same pathways driven by pathophysiological processes and as such cease to provide a protective mechanism and instead contribute to debilitating symptoms associated with a wide range of disease states. Pain is a feature of many trauma and disease states. When a substantial injury, via disease or trauma, to body tissue occurs the characteristics of nociceptor activation are altered. There is sensitisation in the periphery, locally around the injury and centrally where the nociceptors terminate. This leads to hypersensitivity at the site of damage and in nearby normal tissue. In acute pain these mechanisms can be useful and allow for the repair processes to take place and the hypersensitivity returns to normal once the injury has healed. However, in many chronic pain states, the hypersensitivity far outlasts the healing process and is normally due to nervous system injury. This injury often leads to maladaptation of the afferent fibres (Woolf & Salter 2000 Science 288: 1765–1768). Clinical pain is present when discomfort and abnormal sensitivity feature among the patient's symptoms. Patients tend to be quite heterogeneous and may present with various pain symptoms. There are a number of typical pain subtypes: 1) spontaneous pain which may be dull, burning, or stabbing; 2) pain responses to noxious stimuli are exaggerated (hyperalgesia); 3) pain is produced by normally innocuous stimuli (allodynia) (Meyer et al., 1994 Textbook of Pain 13–44). Although patients with back pain, arthritis pain, CNS trauma, or neuropathic pain may have similar symptoms, the underlying mechanisms are different and, therefore, may require different treatment strategies. Therefore pain can be divided into a number of different areas because of differing pathophysiology, these include nociceptive, inflammatory, neuropathic pain etc. It should be noted that some types of pain have multiple aetiologies and thus can be classified in more than one area, e.g. Back pain, Cancer pain have both nociceptive and neuropathic components.

Nociceptive pain is induced by tissue injury or by intense stimuli with the potential to cause injury. Pain afferents are activated by transduction of stimuli by nociceptors at the site of injury and sensitise the spinal cord at the level of their termination. This is then relayed up the spinal tracts to the brain where pain is perceived (Meyer et al., 1994 Textbook of Pain 13–44). The activation of nociceptors activates two types of afferent nerve fibres. Myelinated A-delta fibres transmitted rapidly and are responsible for the sharp and stabbing pain sensations, whilst unmyelinated C fibres transmit at a slower rate and convey the dull or aching pain. Moderate to severe acute nociceptive pain is a prominent feature of, but is not limited to pain from strains/sprains, post-operative pain (pain following any type of surgical procedure), posttraumatic pain, burns, myocardial infarction, acute pancreatitis, and renal colic. Also cancer related acute pain syndromes commonly due to therapeutic interactions such as chemotherapy toxicity, immunotherapy, hormonal therapy and radiotherapy. Moderate to severe acute nociceptive pain is a prominent feature of, but is not limited to, cancer pain which may be tumour related pain, (e.g. bone pain, headache and facial pain, viscera pain) or associated with cancer therapy (e.g. postchemotherapy syndromes, chronic postsurgical pain syndromes, post radiation syndromes), back pain which may be due to herniated or ruptured intervertebral discs or abnormalities of the lumber facet joints, sacroiliac joints, paraspinal muscles or the posterior longitudinal ligament Neuropathic pain is defined as pain initiated or caused by a primary lesion or dysfunction in the nervous system (IASP definition). Nerve damage can be caused by trauma and disease and thus the term 'neuropathic pain' encompasses many disorders with diverse aetiologies. These include but are not limited to, Diabetic neuropathy, Post herpetic neuralgia, Back pain, Cancer neuropathy, HIV neuropathy, Phantom limb pain, Carpal Tunnel Syndrome, chronic alcoholism, hypothyroidism, trigeminal neuralgia, uremia, or vitamin deficiencies. Neuropathic pain is pathological as it has no protective role. It is often present well after the original cause has dissipated, commonly lasting for years, significantly decreasing a patients quality of life (Woolf and Mannion 1999 Lancet 353: 1959–1964). The symptoms of neuropathic pain are difficult to treat, as they are often heterogeneous even between patients with the same disease (Woolf & Decosterd 1999 Pain Supp. 6: S141–S147; Woolf and Mannion 1999 Lancet 353: 1959–1964). They include spontaneous pain, which can be continuous, or paroxysmal and abnormal evoked pain, such as hyperalgesia (increased sensitivity to a noxious stimulus) and allodynia (sensitivity to a normally innocuous stimulus).

The inflammatory process is a complex series of biochemical and cellular events activated in response to tissue injury or the presence of foreign substances, which result in swelling and pain (Levine and Taiwo 1994: Textbook of Pain 45–56). Arthritic pain makes up the majority of the inflammatory pain population. Rheumatoid disease is one of the commonest chronic inflammatory conditions in developed countries and rheumatoid arthritis is a common cause of disability. The exact aetiology of RA is unknown, but current hypotheses suggest that both genetic and microbiological factors may be important (Grennan & Jayson 1994 Textbook of Pain 397–407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder 2002 Ann Pharmacother. 36: 679–686; McCarthy et al., 1994 Textbook of Pain 387–395). Most patients with OA seek medical attention because of pain. Arthritis has a significant impact on psychosocial and physical function and is known to be the leading cause of disability in later life. Other types of inflammatory pain include but are not limited to inflammatory bowel diseases (IBD), Other types of pain include but are not limited to;

Musculo-skeletal disorders including but not limited to myalgia, fibromyalgia, spondylitis, sero-negative (non-rheumatoid) arthropathies, non-articular rheumatism, dystrophinopathy, Glycogenolysis, polymyositis, pyomyositis.

Central pain or 'thalamic pain' as defined by pain caused by lesion or dysfunction of the nervous system including but not limited to central post-stroke pain, multiple sclerosis, spinal cord injury, Parkinson's disease and epilepsy.

Heart and vascular pain including but not limited to angina, myocardial infarction, mitral stenosis, pericarditis, Raynaud's phenomenon, scleredoma, scleredoma, skeletal muscle ischemia.

Visceral pain, and gastrointestinal disorders. The viscera encompasses the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders include the functional bowel disorders (FBD) and the inflammatory bowel diseases (IBD). These GI disorders include a wide range of disease states that are currently only moderately controlled, including—for FBD, gastro-esophageal reflux, dyspepsia, the irritable bowel syndrome (IBS) and functional abdominal pain syndrome (FAPS), and—for IBD, Crohn's disease, ileitis, and ulcerative colitis, which all regularly produce visceral pain. Other types of visceral pain include the pain associated with dysmenorrhea, pelvic pain, cystitis and pancreatitis.

Head pain including but not limited to migraine, migraine with aura, migraine without aura, cluster headache, tension-type headache.

Orofacial pain including but not limited to dental pain, temporomandibular myofascial pain.

The compounds of formula (VI) are also expected to be useful in the treatment of depression. Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales, such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the Diagnostic and Statistical Manual of Mental Disorders (Fourth Edition) referred to as the DSM-IV-R manual published by the American Psychiatric Association, 1994.

The compounds of formula (VI) are also expected to be useful in the treatment of anxiety and of panic as demonstrated by means of standard pharmacological procedures.

The compounds of formula (VI) can be administered, for example but not limited to the following route: orally, buccally or sublingually in the form of tablets, capsules, multi-and nano-particulates, gels, films (incl. mucoadhesive), powder, ovules, elixirs, lozenges (incl. liquid-filled), chews, solutions, suspensions and sprays. The compounds of formula (VI) may also be administered as osmotic dosage form, or in the form of a high energy dispersion or as coated particles or fast-dissolving, fast-disintegrating dosage form as described in Ashley Publications, 2001 by Liang and Chen.

The compounds of formula (VI) can also be administered by injection, that is, intravenously, intramuscularly, intracutaneously, intraduodenally, or intraperitoneally, intraarterially, intrathecally, intraventricularly, intraurethrally, intrasternally, intracranially, intraspinally or subcutaneously, or they may be administered by infusion, needle-free injectors or implant injection techniques.

Also, the compounds of formula (VI) can be administered intranasally or by inhalation.

Alternatively, the compounds of formula (VI) may be administered topically to the skin, mucosa, dermally or transdermally, for example, in the form of a gel, hydrogel, lotion, solution, cream, ointment, dusting powder, dressing, foam, film, skin patch, wafers, implant, sponges, fibres, bandage, microemulsions and combinations thereof.

Alternatively, the compounds of formula (VI) can be administered rectally, for example in the form of a suppository or pessary. They may also be administered by vaginal route.

The compounds of formula (VI) may also be administered by the ocular route. They may also be administered in the ear, using for example but not limited to the drops.

The compounds of formula (VI) may also be used in combination with a cyclodextrin. Alpha-, beta- and gamma-cyclodextrins are the most commonly used and suitable examples and are described in WO-A-91/11172, WO-A-94/02518 and WO-A-98/55148.

The term 'administered' includes delivery by viral or non-viral techniques. Viral delivery mechanisms include but are not limited to adenoviral vectors, adeno-associated viral (AAV) vectors, herpes viral vectors, retroviral vectors, lentiviral vectors, and baculoviral vectors. Non-viral delivery mechanisms include lipid mediated transfection, lipsomes, immunoliposomes, lipofectin, cationic facial amphiphiles (CFAs) and combinations thereof. The routes for such delivery mechanisms include but are not limited to mucosal, nasal, oral, parenteral, gastrointestinal, topical or sublingual routes.

The pharmaceutical preparation of a compound of formula (VI) is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form. The quantity of active component in a unit dose preparation may be varied or adjusted from 0.1 mg to 1 g according to the particular application and the potency of the active component. In medical use the drug may be administered three times daily as, for example, capsules of 100 or 300 mg. In therapeutic use, the therapeutic compounds are administered at the initial dosage of about 0.01 mg to about 100 mg/kg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The pharmaceutical composition of a compound of formula (VI) can, if desired, also contain one or more other compatible therapeutic agents. In particular, the composition can be combined with any one or more compounds useful in the treatment of pain.

General Methods

According to a first process (A), a compound of formula (I) may be prepared by addition of a suitable base to a compound of formula (VII):

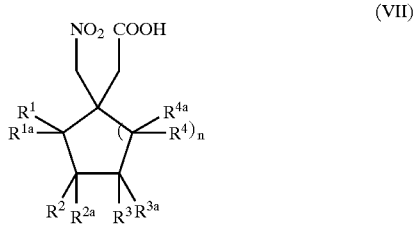

(VII)

The reaction may be carried out in a suitable organic solvent, such as methanol, ethanol isopropanol, diethyl ether or ethyl acetate, at room temperature.

A compound of formula (VII) may be prepared according to scheme 1.

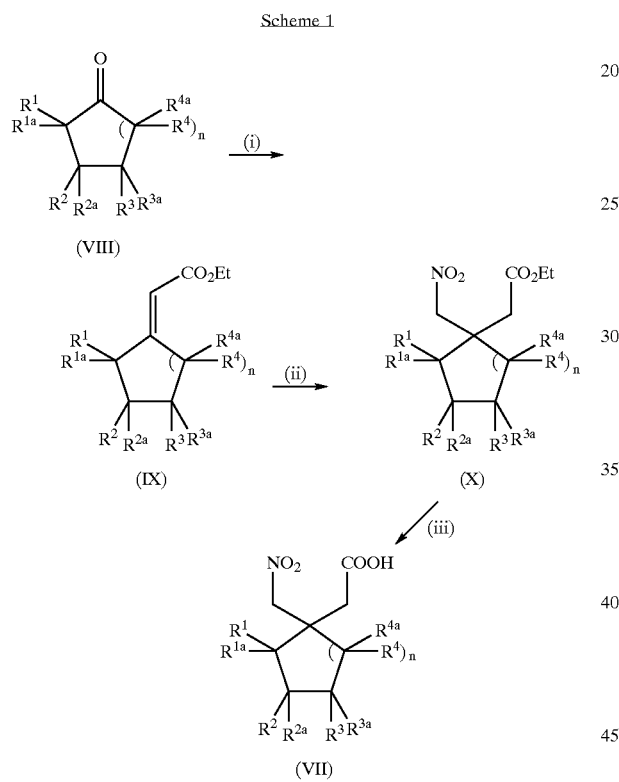

(i) The ketone (VIII) is converted to an unsaturated ester (IX) by reaction with a trialkylphosphonoacetate such as triethylphosphonoacetate in the presence of a base. Suitable bases include sodium hydride, potassium hydride, lithium- or sodium- or potassium-hexamethyldisilazide, butyllithium or potassium tert-butoxide. The reaction may be carried out in a polar aprotic organic solvent such as tetrahydrofuran, dimethylformamide, diethyl ether or dimethylsulfoxide at a temperature in the range from −78° C. to 100° C.

(ii) Nitromethane is added to the unsaturated ester (IX) by a Michael addition reaction in the presence of a base and in a polar aprotic organic solvent at a temperature of −20° C. to 100° C. to give the nitroester (X). Suitable bases include tetrabutylammonium fluoride, tetramethylguanidine, 1,5-diaza-bicyclo[4.3.0]non-5-ene, 1,8-diazabicyclo[5.4.0]undec-7-ene, a sodium or potassium alkoxide such as potassium tert-butoxide, potassium carbonate, sodium hydride or potassium fluoride. Suitable organic solvents include tetrahydrofuran, diethyl ether, dimethylformamide, dimethylsulphoxide, benzene, toluene, dichloromethane, chloroform or tetrachloromethane.

(iii) The nitroester (X) is hydrolysed with a suitable base to give the nitro acid (VII). Suitable bases include sodium hydroxide. Suitable organic solvents include methanol, ethanol, isopropanol, tetrahydrofuran or acetonitrile.

According to a second process (B), compounds of formula (VI) may be prepared from the salts of formula (I) according to Scheme 2.

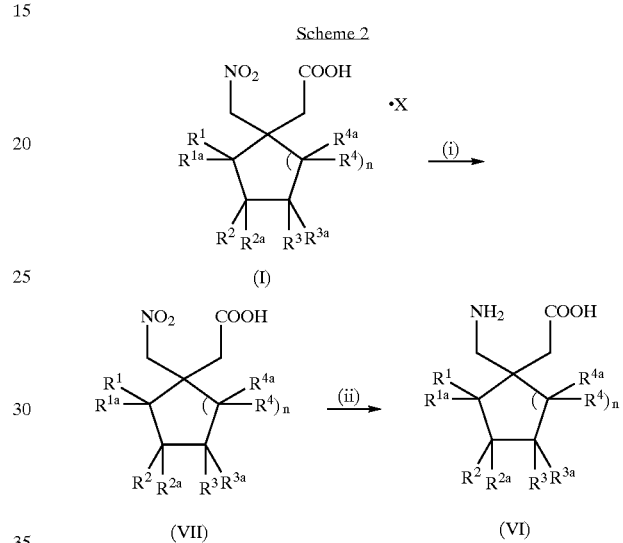

(i) The salt (I) is converted to the free acid (VII) in the presence of a suitable acid. Suitable acids include hydrochloric acid. Suitable organic solvents include dichloromethane, benzene, toluene, diethyl ether or ethyl acetate at room temperature.

(ii) The nitro acid (VII) is reduced by hydrogenation in the presence of a suitable catalyst to give the amino acid (VI). Suitable catalysts include Raney nickel, palladium on charcoal or other rhodium, nickel, platinum or palladium containing catalyst in a solvent such as methanol, ethanol, isopropanol, ethyl acetate, tetrahydrofuran, 1,4-dioxane, chloroform or diethyl ether at a temperature in the range from 20° C. to 100° C.

Referring to the general methods above, it will be readily understood to the skilled person that where protecting groups are present, these will be generally interchangeable with other protecting groups of a similar nature, e.g. where an acid group is described as being protected with an ethyl group, this may be readily interchanged with any suitable alkyl group, suitably any $C_{1-6}$alkyl group.

It will be readily understood to the skilled person that particular steps in the general methods presented herein above may be suitably combined in any other manner not shown to provide a compound according to the present invention.

The present invention is illustrated by the following non-limiting examples and intermediates.

EXAMPLE 1

(1R,5R,6S)-[6-(Nitromethyl)bicyclo[3.2.0]hept-6-yl]
acetic acid cyclohexylamine salt

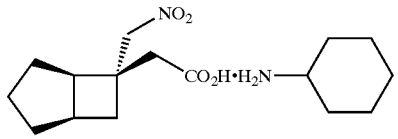

A solution of the nitro acid of preparation 3 (928 g; 4.35 mol) in ethyl acetate (9.6 L) was dried by atmospheric azeotropic distillation at constant volume. After cooling the solution to 40° C., cyclohexylamine (423 g; 4.26 mol) was added over 15 minutes. The resultant slurry was cooled to 20° C. over 4 hours and left to stir for 13 hours at 20° C. The solid was collected by filtration and the damp filter cake washed with ethyl acetate (1.3 L). The isolated solid was then dried in vacuo at 30° C. for 18 hours to give the title compound as a white solid (1.205 Kg) in 91% yield.

Melting point: 140.4–141.6° C. (decomposed)

$^1$H-NMR (400 MHz, $d_6$-DMSO): δ=4.95 (2H, dd), 2.72 (2H, m), 2.20–2.00 (3H, m), 1.90–1.70 (7H, m), 1.55 (1H, m), 1.45–1.00 (10H, m).

EXAMPLE 2

(1R,5R,6S)-[6-(Nitromethyl)bicyclo[3.2.0]hept-6-yl]
acetic acid (R)-α-methylbenzylamine salt

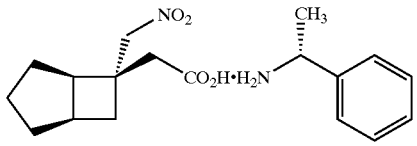

The nitro acid of preparation 3 (5.0 g, 23.4 mmol) was dissolved in ethyl acetate (60 ml) and (R)-α-methylbenzylamine (2.84 g, 23.4 mmol) dissolved in ethyl acetate (10 ml) was added at room temperature. The resultant slurry was stirred for 1 hour. The product was collected by filtration and the damp filter cake washed with ethyl acetate (15 ml). The isolated solid was then dried in vacuo at 40° C. for 2 hours to give the title compound as a white solid (6.31 g).

Melting point: 124.3–124.9° C. (decomposed)

$^1$H-NMR (400 MHz, $d_6$-DMSO): δ=7.40–7.20 (5H, m), 5.00–4.80 (2H, dd), 4.10 (1H, q), 2.75 (1H, m), 2.25 (2H, dd), 2.05 (1H, m), 1.80–1.65 (3H, m), 1.50–1.25 (8H, m).

EXAMPLE 3

(1R,5R,6S)-[6-(Nitromethyl)bicyclo[3.2.0]hept-6-yl]
acetic acid

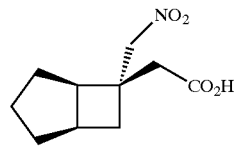

The (R)-α-methylbenzylamine salt of the nitro acid from example 2 (5.0 g, 23.4 mmol) was added to a mixture of ethyl acetate (50 ml) and 2M hydrochloric acid (15 ml). The mixture was stirred vigorously for 3–4 minutes and the phases were separated. The organic layer was further washed with 2M hydrochloric acid (15 ml) and demineralised water (15 ml). The organic layer was separated and the solvent was removed in vacuo to give the title compound as a yellow oil, which rapidly crystallised on standing (3.49 g).

Melting point: 64–66° C.

$^1$H-NMR (400 MHz, $CDCl_3$): δ=4.80 (2H, dd), 2.85 (1H, m), 2.60 (3H, m), 2.15 (1H, m), 1.90 (1H, m), 1.80–1.70 (2H, m), 1.60–1.40 (4H, m).

EXAMPLE 4

[(1R,5R,6S)-6-(Aminomethyl)bicyclo[3.2.0]hept-6-yl]acetic acid

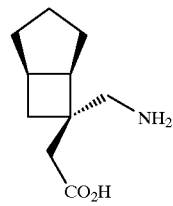

The cyclohexylamine salt of the nitro acid from example 1 (100 g; 320 mmol) was added to a mixture of ethyl acetate (680 ml) and a 2M aqueous solution of hydrochloric acid (340 ml). The mixture was stirred vigorously for 10 minutes and the phases were separated. The organic layer was further washed with demineralised water (340 ml). The organic layer was separated and demineralised water (1360 ml) was added. To this two phase mixture 5% platinum on carbon as a 50% water wet catalyst (13.65 g) was added. The reaction mixture was then hydrogenated at 50° C. and a hydrogen pressure of 150 psi for 24 hours. The hydrogen was purged with nitrogen and the reaction mixture was heated to 70° C. The reaction mixture was filtered through Celite at 70° C. and the filter pad was washed with hot demineralised water (50 ml). The filtrate was allowed to settle, the phases were separated at 70° C. and the lower aqueous phase was removed and concentrated by distillation at atmospheric pressure to a sixth of its original volume. The white slurry was cooled to 50° C. and isopropanol (705 ml) was then added over a period of 1.7 hours. The white slurry was then cooled to between +5° C. and +10° C. over 90 minutes and stirred for 2.5 hours. The solid was collected by filtration and the damp filter cake washed with isopropanol (60 ml). The isolated solid was then dried in vacuo at 45° C. for 18 hours to give the title compound in high purity as a white crystalline solid (36.3 g) in 62% yield.

$^1$H-NMR (400 MHz, $d_6$-DMSO): δ=7.94 (3H, br s), 3.15 (1H, d), 3.07 (1H, d), 2.72 (1H, quin), 2.46 (1H, m), 2.42 (1H, d), 2.33 (1H, d), 1.98 (1H, m), 1.80–1.64 (2H, m), 1.59 (1H, m), 1.48–1.28 (3H, m), 1.23 (1H, dd).

$[α]_D$(c=0.127 in methanol)=−12.4°

Melting Point (Perkin Elmer DSC7): 198° C.

EXAMPLE 5

(1R,5R,6S)-[6-(Nitromethyl)bicyclo[3.2.0]hept-6-yl]
acetic acid sodium salt

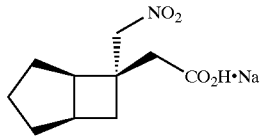

The nitro acid of preparation 3 (750 mg, 3.52 mmol) was dissolved in ethyl acetate (5 ml) and sodium hydroxide (141 mg, 3.52 mmol) dissolved in demineralised water (3 ml) was added at room temperature. The resultant mixture was stirred vigorously. The solvents are removed in vacuo and the residue was dried by the addition of toluene which was removed in vacuo, this process was repeated several times until all water had been removed from the residue. This gave the title compound as a beige solid (666 mg).

Melting point: broad, 110.0–117.9° C. (decomposed)

$^1$H-NMR (400 MHz, $d_6$-DMSO): δ=5.05 (2H, br d), 2.65 (1H, m), 2.05 (3H, m), 1.80–1.60 (3H, m), 1.45–1.20 (5H, m).

EXAMPLE 6

(1RS,5RS,6SR)-[6-(Nitromethyl)bicyclo[3.2.0]hept-6-yl]acetic acid (R)-α-methylbenzylamine salt

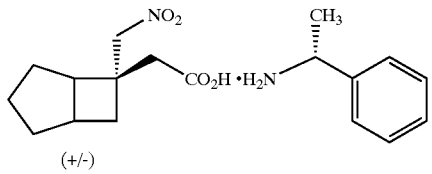
(+/-)

The racemic nitro acid prepared using a similar method to that of preparation 3 (1.50 g, 7.04 mmol) was dissolved in ethyl acetate (12 ml) and (R)-α-methylbenzylamine (0.85 g, 7.01 mmol) dissolved in ethyl acetate (5 ml) was added at room temperature. The resultant slurry was stirred overnight. The product was collected by filtration and the damp filter cake washed with ethyl acetate (5 ml). The isolated solid was then dried in vacuo at 40° C. for 4 hours to give the title compound as a solid (1.73 g).

$^1$H-NMR (400 MHz, $d_6$-DMSO): δ=7.40–7.20 (5H, m), 5.00–4.80 (2H, dd), 4.10 (1H, q), 2.75 (1H, m), 2.25 (2H, dd), 2.05 (1H, m), 1.80–1.65 (3H, m), 1.50–1.25 (8H, m).

EXAMPLE 7

(1RS,5RS,6SR)-[6-(Nitromethyl)bicyclo[3.2.0]hept-6-yl]acetic acid (S)-α-methylbenzylamine salt

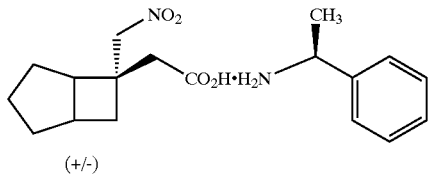
(+/-)

The racemic nitro acid, prepared using a similar method to that of preparation 3 (1.50 g, 7.04 mmol) was dissolved in ethyl acetate (12 ml) and (S)-α-methylbenzylamine (0.85 g, 7.01 mmol) dissolved in ethyl acetate (5 ml) was added at room temperature. The resultant slurry was stirred overnight. The product was collected by filtration and the damp filter cake washed with ethyl acetate (5 ml). The isolated solid was then dried in vacuo at 40° C. for 4 hours to give the title compound as a solid (1.73 g).

$^1$H-NMR (400 MHz, $d_6$-DMSO): δ=7.40–7.20 (5H, m), 5.00–4.80 (2H, dd), 4.10 (1H, q), 2.75 (1H, m), 2.25 (2H, dd), 2.05 (1H, m), 1.80–1.65 (3H, m), 1.50–1.25 (8H, m).

EXAMPLE 8

(1RS,5RS,6SR)-[6-(Nitromethyl)bicyclo[3.2.0]hept-6-yl]acetic acid (S)-1-cyclohexylethylamine salt

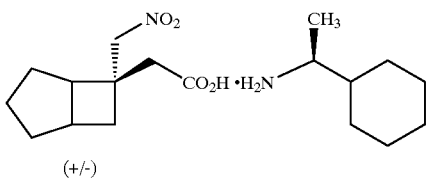
(+/-)

The racemic nitro acid, prepared using a similar method to that of preparation 3, (1.50 g, 7.04 mmol) was dissolved in ethyl acetate (12 ml) and (S)-1-cyclohexylethylamine (0.90 g, 7.07 mmol) dissolved in ethyl acetate (5 ml) was added at room temperature. The resultant slurry was stirred overnight. The product was collected by filtration and the damp filter cake washed with ethyl acetate (5 ml). The isolated solid was then dried in vacuo at 40° C. for 4 hours to give the title compound as a solid (1.58 g).

$^1$H-NMR (400 MHz, $d_6$-DMSO): δ=4.94 (2H, dd), 2.81–2.67 (2H, m), 2.16 (2H, dd), 2.08–2.02 (1H, m), 1.75–1.60 (8H, m), 1.43–1.26 (5H, m), 1.18–0.89 (8H, m).

EXAMPLE 9

(1RS,5RS,6SR)-[6-(Nitromethyl)bicyclo[3.2.0]hept-6-yl]acetic acid cinchonidine salt

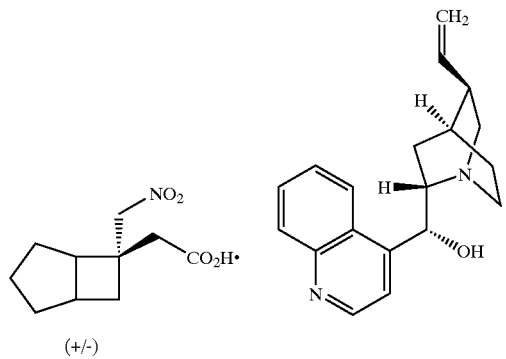
(+/-)

The racemic nitro acid, prepared using a similar method to that of preparation 3, (1.50 g, 7.04 mmol) was dissolved in ethyl acetate (12 ml) and cinchonidine (2.07 g, 7.03 mmol) dissolved in ethyl acetate (5 ml) was added at room temperature. The resultant slurry was stirred overnight. The product was collected by filtration and the damp filter cake washed with ethyl acetate (5 ml). The isolated solid was then dried in vacuo at 40° C. for 4 hours to give the title compound as a solid (2.78 g).

$^1$H-NMR (400 MHz, $d_6$-DMSO): δ=8.81 (1H, d), 8.28 (1H, d), 8.00 (1H, m), 7.71 (1H, m), 7.58 (1H, m), 7.54 (1H, d), 5.85 (1H, m), 5.33 (1H, d), 5.01–4.80 (4H, m), 3.22 (1H, m), 3.12 (1H, m), 2.88 (1H, m), 2.77 (1H, m), 2.53 (1H, m) 2.45 (2H, m), 2.23 (1H, m), 2.07 (1H, m), 1.77–1.62 (6H, m), 1.48–1.33 (4H, m).

PREPARATION 1

Ethyl (2E)-(1R,5R)-bicyclo[3.2.0]hept-6-ylidene acetate/ethyl (2Z)-(1R,5R)-bicyclo[3.2.0]hept-6-ylidene acetate

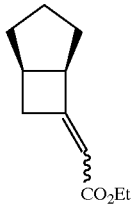

Triethylphosphonoacetate (1.88 Kg; 8.40 mol) was added to a suspension of sodium ethoxide (0.524 Kg; 7.70 mol) in n-heptane (3.1 L) over 0.5 hours, maintaining the temperature between −10° C. and 0° C. The reaction mixture was then stirred at −10° C. for 0.3 hours. A solution of (1R,5R)-bicyclo[3.2.0]heptan-6-one (0.771 Kg; 7.00 mol) in n-heptane (9.2 L) was added over 3 hours maintaining the temperature between −12° C. and −8° C. The reaction mixture was stirred at −10° C. for 1.5 hours, then a 2M aqueous solution of hydrochloric acid (6 L) was added rapidly causing the reaction temperature to rise to +5° C. The reaction mixture was warmed to +25° C. and the phases were separated. The organic layer was washed with a 2M aqueous solution of sodium carbonate (6 L) followed by sodium chloride (0.2 Kg) dissolved in demineralised water (6 L). The organic layer (approximately 12.5 L in volume) containing the title compound (0.921 Kg) was used directly in the next step.

$^1$H-NMR (400 MHz, CDCl$_3$): δ=5.55 (1H, d), 4.15 (2H, q), 3.40 (1H, m), 3.20 (1H, m), 2.90 (1H, m), 2.55 (1H, m), 1.8–1.5 (5H, m), 1.30 (3H, t).

PREPARATION 2

Ethyl (1R,5R,6S)-[6-(Nitromethyl)bicyclo[3.2.0] hept-6-yl]acetate

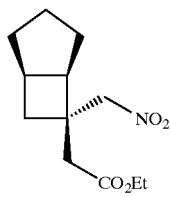

The n-heptane solution of the compound of preparation 1 (0.921 Kg; 5.11 mol) was concentrated by distillation at atmospheric pressure to 36% of its original volume. The n-heptane was then replaced with tetrahydrofuran by atmospheric azeotropic distillation at constant volume. The reaction mixture was cooled to 20–25° C., then tetrabutylammonium fluoride trihydrate (2.10 Kg; 6.64 mol) and nitromethane (0.499 Kg, 8.18 mol) were added. The resulting brown solution was stirred at 20–25° C. for 17 hours. To the reaction mixture a 2M aqueous solution of hydrochloric acid (4.5 L) was added, causing the reaction temperature to rise by 8° C. n-heptane (4.5 L) was added and the phases were separated. The organic layer was then washed with demineralised water (4.5 L) to give the title product (1.08 Kg) in 88% yield as an organic solution which is used directly in the next step.

$^1$H-NMR (400 MHz, CDCl$_3$): δ=4.80 (2H, m), 4.15 (2H, m), 2.85 (1H, m), 2.65 (1H, m), 2.55 (2H, m), 2.20 (1H, m), 1.9–1.4 (7H, m), 1.25 (3H, t).

PREPARATION 3

(1R,5R,6S)-[6-(Nitromethyl)bicyclo[3.2.0]hept-6-yl] acetic acid

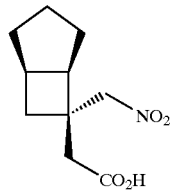

The n-heptane from the organic solution of the nitro ester of preparation 2 (1.08 Kg; 4.49 mol) was replaced with tetrahydrofuran by azeotropic distillation at atmospheric pressure and constant volume. The solution was cooled to +25° C. and a solution of sodium hydroxide (0.359 Kg; 8.98 mol) in demineralised water (4.5 L) was added and the reaction stirred for 16 hours. n-heptane (4.5 L) was added and the phases were separated. The aqueous phase was adjusted to pH 2–4 by the addition of concentrated hydrochloric acid (0.8 L) giving a suspension. The aqueous phase was extracted with ethyl acetate (9.6 L) to give the title product (0.928 Kg) in 97% yield as an organic solution which is used directly in the next step.

$^1$H-NMR (400 MHz, CDCl$_3$): δ=4.80 (2H, m), 2.85 (1H, m), 2.60 (3H, m), 2.20 (1H, m), 1.85 (1H, m), 1.70 (2H, m), 1.6–1.4(4H, m).

PREPARATION 4

(1α,3α,5α)-[3-(nitromethyl)bicyclo[3.2.0]hept-3-yl] acetic acid

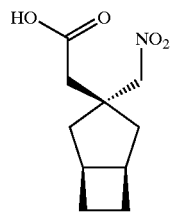

50 g of ethyl (1α,3α,5α)-[3-(nitromethyl)bicyclo[3.2.0] hept-3-yl]acetate was suspended in a mixture of 250 mL 2M NaOH and 50 mL of MeOH. The reaction mixture was stirred for 1.5 hr at 60° C. After this time the methanol was distilled off under reduced pressure. The aqueous solution was acidified with 6M HCl, forming a white precipitate. The aqueous phase was extracted 4 times with 560 mL MTBE each. The combined organic phases were dried over Na$_2$SO$_4$ and concentrated under reduced pressure. The crystalline residue was dried in an air circulating dryer at 40° C. to constant weight. The crude product was recrystallized from n-heptane to give 21.4 g of the title compound.

(HPLC: 93.7 rel %; Mp.: 84.9° C.)

PREPARATION 5

(1α,3α,5α)-[3-(aminomethyl)bicyclo[3.2.0]hept-3-yl]acetic acid

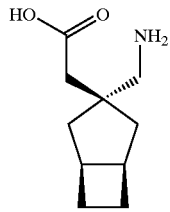

1.82 g of (1α,3α,5α)-[3-(nitromethyl)bicyclo[3.2.0]hept-3-yl]acetic acid (HPLC-purity: 93.73 rel %) was dissolved in 117 mL of MeOH and hydrogenated over 2.4 g of Ra—Ni at 90° C. and 8 bar. After filtration, the solvent was distilled off under reduced pressure, yielding 1.52 g (97.4%). 1.52 g of crude product was recrystallized from 35 mL of water. After cooling to room temperature, the precipitated product was filtered off. The aqueous mother liquor was concentrated to dryness, yielding 1.19 g of the title compound.

What is claimed is:

1. A compound of formula (III):

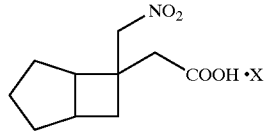

(III)

wherein X is a basic counterion selected from a group I or group II metal and a primary, secondary or tertiary amine.

2. A compound according to claim 1, which is of formula (IIIa):

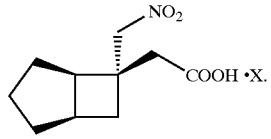

(IIIa)

3. A compound according to claim 2 wherein X is selected from sodium, cinchonidine, cyclohexylammonium, R-alpha-methylbenzylammonium, S-alpha-methylbenzylammonium and S-2-cyclohexylethylammonium.

4. A process for the preparation of a compound of formula (IIIa)

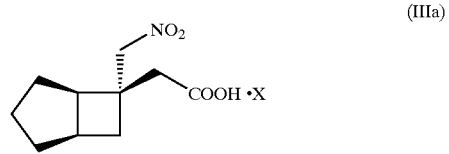

(IIIa)

by addition of the base to a compound of formula (VIIa) in a suitable solvent:

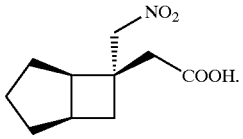

(VIIa)

5. A process for the preparation of (1R,5R,6S)-[6-(aminomethyl)bicyclo[3.2.0]hept-6-yl]acetic acid, comprising a) conversion of a compound according to claim 2 to the corresponding free nitro acid in the presence of a suitable acid; followed by b) reduction of the nitro group by hydrogenation in the presence of a suitable catalyst.

* * * * *